United States Patent [19]

Krenzer et al.

[11] Patent Number: 4,758,263

[45] Date of Patent: Jul. 19, 1988

[54] 2-(2,5-DIFLUOROPHENYL)-4-METHYL-1,2,4-OXADIAZOLIDINE-3,5 DIONES

[75] Inventors: John Krenzer, Oak Park; Leonard J. Stach, Riverside, both of Ill.

[73] Assignee: Sandoz Ltd., Basel, Switzerland

[21] Appl. No.: 923,457

[22] Filed: Oct. 27, 1986

[51] Int. Cl.$^4$ .................. C07D 271/06; A01N 43/82
[52] U.S. Cl. ......................................... 71/92; 548/132
[58] Field of Search ............................ 548/132; 71/92

[56] References Cited

U.S. PATENT DOCUMENTS 3,437,664  4/1969  Krenzer .............................. 548/132

Primary Examiner—Robert Gensil

Attorney, Agent, or Firm—Gerald D. Sharkin; Richard E. Vila

[57] ABSTRACT

Disclosed are herbicides of the formula:

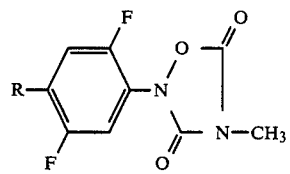

wherein R is H or halo of atomic weight of from 18 to 80.

10 Claims, No Drawings

2-(2,5-DIFLUOROPHENYL)-4-METHYL-1,2,4-OXADIAZOLIDINE-3,5 DIONES

The present invention to 2-(2,5-difluorophenyl)-4-methyl-1,2,4-oxadiazolidine-3,5-diones, their use as a herbicide and agricultural compositions containing the same.

Herbicidal 2-phenyl-1,2,4-oxadiazolidines have been previously described, for example, in U.S. Pat. No. 3,437,664. Among the compounds originated in connection with such prior invention, the compound 2-(3,4-dichlorophenyl)-4-methyl-1,2,4-oxadiazolidine-3,5-dione (also known as PROBE ®) was found to be of the greater interest and has been subjected to commercial development for use as a herbicide, particularly, for example, as a herbicide for use in cotton by post-emergence directed spray application.

The present invention provides compounds of the formula I:

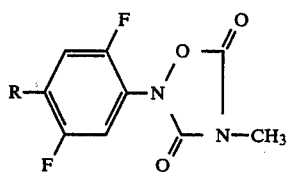

wherein R is H or halo of atomic weight of from 18 to 80.

The compounds of the formula I provided by the invention are useful as herbicides and are indicated to have a desirable broad spectrum of high herbicidal activity, particularly on pre-emergence application.

The compounds of the formula I may be prepared by Procedure A by reacting a compound of the formula II:

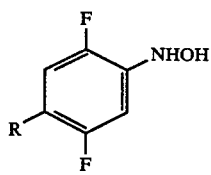

wherein R is above defined, with the compound of the formula III:

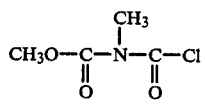

Procedure A may be carried out at temperature in the range from minus 10° C. to 80° C., preferably from plus 10° C. to 50° C., in an inert solvent media such as in an alkanol, eg. methanol. The product of the formula I may be isolated and recovered from the reaction mixture of Procedure A by working up by established procedures.

The compound of the formula III is known. The compounds of the formula II are of known type and may be prepared by reduction of the corresponding nitro compound of the formula IV.

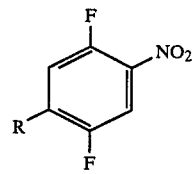

wherein R is as above defined, as described in Example 1, below.

The compounds of the formula IV are also of known type and may be prepared by established procedures, such as by nitration of the known compound 1,4-difluorobenzene, as described in Example 1, below.

In the compounds of the formula I, R is preferably H, fluoro or chloro, more preferably H or chloro, and desirably H.

The compounds of the formula I are useful becuase they control the growth of plants. By plants it is meant germinating seeds, emerging seedlings and established vegetation including underground portions. In particular, the compounds are useful as herbicides as indicated by causing damage to both monocotyledoneous and dicotyledoneous plants in various standard evaluations for determining such effects. Such herbicidal effects indicate that the compounds of the formula I are particularly of interest in combatting weeds (unwanted plants) in a locus in which such weeds are present.

The compounds of the formula I are also indicated to be somewhat stronger acting against dicotyledeneous plants than monocotyledoneous plants. Relatively less toxicity towards crops than towards weeds is further indicated. Hence, the compounds are also of particular interest as selective herbicides to combat weeds in a crop locus, for example, in a locus of a crop such as corn (maize), rice, sorghum and cotton, especially corn.

The present invention therefore also provides a method of combating weeds in a locus which comprises applying to the locus a herbicidally effective amount of a compound of the invention. When use is desired in a crop locus, the amount applied will be sufficient to combat weeds without substantially damaging the crop.

For general herbicidal as well as selective herbicidal use of the compounds of the invention, the particular amounts to be applied will vary depending upon recognized factors such as the compound employed, the plants primarily in the locus, the timing, mode and formulation of application, the various conditions of treatment such as soil and weather and the like. However, in general, satisfactory results in weed control are usually obtained upon application of the compounds of the invention at a rate in the range of from 0.1 to 10 Kg./hectare, more usually 0.3 to 5 Kg./hectare, and preferably 0.5 to 3 Kg./hectare, the application being repeated as necessary. When used in crops, the application usually will not exceed about 5 Kg./hectare, and is usually in the range of 0.1 to 4 Kg./hectare, preferably 0.2 to 3 Kg./hectare.

For practical use as heribicides, the compounds of the formula I may be and are preferably employed in herbicidal compositions comprising a herbicidal effective amount of the compound and an inert carrier which is agriculturally acceptable in the sense of not, by reason of its presence, poisoning the agricultural environment including the immediate soil of application or any crops present therein or otherwise being unsafe for application. Such compositions or formulations may contain 0.01% to 99% by weight of active ingredient, from 0 to 20% by weight of agriculturally acceptable surfactants and 1 to 99.9% by weight of the inert carrier. Higher ratios of surfactant to active ingredient are sometimes desirable and are achieved by incorporation into the formulation or by tank mixing. Application forms of composition typically contain between 0.01 to 25% by weight of active ingredient, but lower or higher levels of active ingredient can, of course, be present depending on the intended use and the physical properties of the compound. Concentrate forms of composition intended to be diluted before use generally contain between 2 and 90%, preferably between 10 and 80% by weight of active ingredient.

Useful compositions or formulations of the compounds of the invention include dusts, granules, pellets, suspension concentrates, wettable powders, emulsifiable concentrates and the like. They are obtained by conventional manner, e.g. by mixing the compounds of the invention with the inert carrier. More specifically, liquid compositions are obtained by mixing the ingredients, fine solid compositions by blending and, usually grinding, suspensions by wet milling and granules and pellets by impregnating or coating (preformed) granular carriers with the active ingredient or by agglomeration techniques.

For example, dusts can be prepared by grinding and blending the active compounds with a solid inert carrier such as the talcs, clays, silicas, pyrophyllite and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water or oil to any desired concentration of the active compound, can be prepared by incorporating wetting agents into concentrated dust compositions.

Alternatively, the compounds of the invention may be used in microencapsulated form.

Agriculturally acceptable additives may be employed in the herbicidal compositions to improve the performance of the active ingredient and to reduce foaming, caking and corrosion.

surfactant as used herein means agriculturally acceptable material which imparts emulsifiability, spreading, wetting, dispersibility or other surface-modifying properties. Examples of surfactants are sodium lignin sulphonate and lauryl sulphate.

Carriers as used herein mean a liquid or solid material used to dilute a concentrated material to a usable or desirable strength. For dusts or granules it can be e.g. talc, kaolin or diatomaceous earth, for liquid concentrate forms, a hydrocarbon such as xylene or an alcohol such as isopropanol; and for liquid application forms, e.g. water or diesel oil.

The compositions of this invention can also comprise other compounds having biological activity, e.g. compounds having similar or complementary herbicidal activity or compounds having antidotal, fungicidal or insecticidal activity.

A typical herbicidal composition, according to this invention, is illustrated by the following Examples A, B and C in which the quantities are in parts by weight.

EXAMPLE A

Preparation of a Dust

Product of Example 1: 10
Powdered Talc: 90.

The above ingredients are mixed in a mechanical grinder-blender and are ground until a homogeneous, free-flowing dust of the desired particle size is obtained. This dust is suitable for direct application to the site of the weed infestation.

EXAMPLE B

Preparation of Wettable Powder 25 parts of a compound of formula I, e.g. the compound of Example 1 hereinafter, are mixed and milled with 25 parts of synthetic fine silica, 2 parts of sodium lauryl sulphate, 3 parts of sodium ligninsulphonate and 45 parts of finely divided kaolin until the mean particle size is about 5 micron. The resulting wettable powder is diluted with water before use to a spray liquor with the desired concentration.

EXAMPLE C

Preparation of Emulsifiable Concentrate (EC)

21 parts of the compound of Example 1 are mixed with 79.5 parts of liquid organic hydrocarbons obtained under the trade designation Isophorone and the resulting solution is then thoroughly mixed with 1.43 parts of the surfactant preparation obtained under the trademark SPONTO N139B and 6.76 parts of the surfactant preparation obtained under the trademark SPONTO AD6-39A. The resulting emulsifiable concentrate is diluted water to the desired concentration for use.

EXAMPLE 1

2-(2,5-Difluorophenyl)-4-methyl-1,2,4-oxadiazolidine-3,5-dione

Step A 1,4-Difluoro-2-nitrobenzene

To a cooled solution (0°–5° C./−15° C. with $CO_2$/acetone/water) of conc. sulfuric acid (600 ml) and 90% nitric acid (330 ml) in a three-necked flask equipped with a mechanical stirrer and thermometer was added 1,4-difluorobenzene dropwise (300 g., 2.63 moles) over 2.5 hours. After an additional 30 min. stirring, the mixture was carefully poured into ice and extracted with ethyl ether (3×600 ml). The organic layers were washed with brine, water, 5% sodium bicarbonate solution, dried over ($Na_2SO_4$) and evaporated in vacuo. The orange liquid was distilled under vacuum to obtain 1,4-difluoro-2-nitrobenzene, b.p. 102°–105° C. at 30 torr.

Step B 1,4-Difluoro-2-hydroxylamine

In a 500 ml. Parr bottle was added 40 g. (0.25 mol) of 1,4-difluoro-2-nitrobenzene, 1.5 g. of 1% Pt/C, 1 ml DMSO, 1 ml $H_2O$, and then 170 ml of methanol. The mixture was evacuated and flushed with hydrogen twice before the hydrogen pressure was brought to 45 psi. The shaker was started along with the air condenser. When 2 equivalents of hydrogen were taken up in about 1 hour, the reaction was stopped and purged with argon. The catalyst was then quickly filtered off with the aid of Celite to obtain a solution of the desired hydroxylamine.

Step C

2-(2,5-Difluorophenyl)-4-methyl-1,2,4-oxadiazolidine-3,5-dione

The solution of 1,4-difluoro-2-hydroxylamine obtained in Step B, above, was transferred to a one liter, three-necked round bottom flask equipped with a magnetic stir bar, addition funnel and thermometer. The solution was cooled to 5° C. with an ice bath and N-chloroformyl-N-chloromethyl-methyl carbamate (38 g., 1 eq) was added dropwise while the temperature was maintained at 10° C. After 12 hours stirring at room temperature, the crude solid product was collected, washed with hexane, and recrystallized from ether to obtain the heading compound, m.p. 66°-68° C. Additional product was obtained when the filtrates were evaporated down and taken up in dichloromethane and water, the organic layer washed with water and dried, the solvent removed, and the crude solid recrystallized with methanol hexane to again obtain the heading compound, m.p. 66°-68° C.

EXAMPLE 2

Following the procedure of Example 1, there was also prepared the compound 2-(4-chloro-2,5-difluorophenyl)-4-methyl-1,2,4-oxadiazolidine-3,5-dione, m.p. 128°-129° C.

The herbicidal activity of the compounds of the invention may be demonstrated and compared with that of other 2-phenyl-4-methyl-1,2,4-oxadiazolidine-3,5-diones by established testing techniques conducted in the greenhouse or open field by testing on spray application of diluted aqueous compositions by pre-emergence and post-emergence application.

In Tables 1 and 2, below, the results obtained in greenhouse evaluations on both pre-emergence and post-emergence testing on a variety of plants are given. In the pre-emergence experiments small plastic greenhouse pots filled with dry soil were seeded with the various weed seeds. Twenty-four hours or less after the seeding, the pots were sprayed with water until the soil was wet and the test compounds formulated as aqueous emulsions were sprayed at the indicated rates on the surface of the soil. After spraying, the soil containers were placed in the greenhouse and provided with supplementary heat as required and daily or more frequent watering. The plants were maintained under these conditions for 21 days, at which time the condition of the plants and the degree of injury to the plants was rated on a scale of from 0 to 10, as follows: 0=no injury, 1, 2=slight injury 3, 4=moderate injury, 5, 6=moderately severe injury, 7, 8, 9=severe injury, 10=death and NE indicated not emerged. In the post-emergence experiments the compounds to be tested were formulated as aqueous emulsions and sprayed at the indicated dosage on the foliage of the various weed species that have attained a prescribed size. After spraying, the plants were placed in a greenhouse and watered daily or more frequently. Water was not applied to the foliage of the treated plants. The severity of the injury was determined 14 days after treatment and was rated on the scale of from 0 to 10 heretobefore described. The aqueous emulsions used in greenhouse testing were prepared by diluting with water an emulsion concentrate containing the active ingredient and 2 parts of dimethylformamide, 4 parts of ethanol, 93.5 parts of acetone and 0.5 parts of surfactant.

In Table 3, below, there are reported the results obtained in small plot field tests in which the active compounds were applied broadcast using a dilute aqueous composition of the active ingredient that had been prepared from the emulsifiable concentrate of Example C, above. The same evaluation was conducted at four different locations within the United States and the mean average results of the four locations are reported in Table 3 using the same 0 to 10 rating system described above. Such evaluation was made 30 days after application of the active ingredient.

In Tables 1, 2 and 3, below, the compound A is the compound of Example 1, above, the compound B is PROBE ®; the compound C is the compound of Example 2, above, and the compound D is the compound 2-(2,5-dichlorophenyl)-4-methyl-1,2,4-oxadiazolidine-3,5-dione (the chloro analogue of the compound of Example 1).

TABLE 1

Pre-emergence Herbicidal Activity
Compounds A, B, C and D

| | Rate of Application (lbs./acre) | | | | | | | |
|---|---|---|---|---|---|---|---|---|
| | Compound A | | Compound B | | Compound C | | Compound D | |
| Plant | 0.5 | 0.25 | 0.5 | 0.25 | 0.5 | 0.25 | 2.0 | 1.0 |
| Velvetleaf | 10 | 10 | 0 | 0 | 10 | 10 | 2 | 0 |
| Pigweed | NE | 8 | NE | 4 | 10 | 9 | 6 | 4 |
| Wild Mustard | 10 | 10 | 10 | 1 | 10 | 0 | 10 | 5 |
| Bindweed | 10 | 8 | 0 | 0 | 10 | 5 | — | — |
| Jimsonweed | 10 | 10 | 1 | 0 | NE | 10 | 1 | 0 |
| Morningglory | 10 | 10 | 0 | 0 | 2 | 0 | 3 | 1 |
| Cotton | 8 | 0 | 0 | 0 | 0 | 0 | 10 | 9 |
| Soybeans | 10 | 7 | 0 | 0 | 0 | 0 | 10 | 9 |
| Sorghum | 7 | 0 | 0 | 0 | 3 | 0 | 7 | 5 |
| Wild Oats | 10 | 10 | 0 | 0 | 10 | 0 | 0 | 0 |
| Cheatgrass | 9 | 8 | 0 | 0 | 3 | 0 | 0 | 0 |
| Yellow Nutsedge | 0 | 0 | 0 | 0 | 0 | 0 | 0 | 0 |
| Crabgrass | 9 | NE | 3 | 0 | 4 | 0 | 3 | 2 |
| Barnyard Grass | 10 | 6 | 0 | 0 | 9 | 0 | 2 | 0 |
| Yellow Foxtail | 9 | 1 | 9 | 0 | 9 | 6 | 0 | 0 |
| Johnson Grass | 7 | 7 | 0 | 0 | 8 | 0 | 0 | 0 |
| Sprangletop | 5 | 2 | 0 | 0 | 2 | 0 | — | — |
| Alfalfa | 9 | 3 | 0 | 0 | 0 | 0 | — | — |
| Rice | 3 | 0 | 0 | 0 | 2 | 0 | — | — |
| Corn | 2 | 0 | 0 | 0 | 0 | 0 | — | — |
| Oats | 10 | 8 | 0 | 0 | 9 | 0 | — | — |
| Wheat | 10 | 8 | 0 | 0 | 10 | 0 | — | — |
| Pintobean | 10 | 8 | 0 | 0 | 0 | 0 | — | — |

TABLE 2

Post-emergence Herbicidal Activity
Compounds A, B, C and D

| | Rate of Application (lbs./acre) | | | | | | | |
|---|---|---|---|---|---|---|---|---|
| | Compound A | | Compound B | | Compound C | | Compound D | |
| Plant | 0.5 | 0.25 | 0.5 | 0.25 | 0.5 | 0.25 | 2.0 | 1.0 |
| Velvetleaf | 10 | 10 | 10 | 10 | 10 | 7 | — | — |
| Pigweed | 10 | 10 | 10 | 10 | 10 | 10 | 8 | 8 |
| Wild Mustard | 10 | 10 | 10 | 10 | 10 | 10 | 9 | 5 |
| Bindweed | 9 | 4 | 10 | 10 | 8 | 4 | 3 | 3 |
| Jimsonweed | 10 | 10 | 10 | 10 | 10 | 10 | 4 | 2 |
| Morningglory | 10 | 7 | 10 | 10 | 9 | 3 | 4 | 3 |
| Wild Oats | 8 | 1 | 1 | 0 | 1 | 0 | 0 | 0 |
| Cheatgrass | 0 | 1 | 0 | 0 | 4 | 0 | — | — |
| Yellow Nutsedge | 0 | 0 | 0 | 0 | 0 | 0 | 0 | 0 |
| Crabgrass | 8 | 0 | 10 | 10 | 3 | 0 | 4 | 0 |
| Barnyard | 0 | 0 | 8 | 0 | 8 | 3 | 3 | 2 |

TABLE 2-continued

Post-emergence Herbicidal Activity
Compounds A, B, C and D

| | Rate of Application (lbs./acre) | | | | | | | |
|---|---|---|---|---|---|---|---|---|
| | Compound A | | Compound B | | Compound C | | Compound D | |
| Plant | 0.5 | 0.25 | 0.5 | 0.25 | 0.5 | 0.25 | 2.0 | 1.0 |
| Grass Yellow Foxtail | 10 | 7 | 10 | 10 | 10 | 5 | 5 | 1 |
| Johnson Grass | 7 | 5 | 7 | 0 | 8 | 3 | 5 | 2 |
| Soybeans | 9 | 3 | 9 | 3 | 7 | 3 | 3 | 4 |
| Cotton | 4 | 1 | 7 | 0 | 7 | 4 | — | — |
| Pintobean | 9 | 6 | 10 | 7 | 10 | 4 | — | — |
| Alfalfa | 2 | 0 | 0 | 10 | 0 | 0 | — | — |
| Wheat | 9 | 3 | 1 | 0 | 6 | 0 | — | — |
| Rice | 8 | 7 | 0 | 0 | 7 | 3 | — | — |
| Sorghum | 3 | 0 | 4 | 1 | 7 | 0 | — | — |
| Corn | 2 | 0 | 0 | 0 | 4 | 1 | — | — |
| Oats | 6 | 1 | 1 | 0 | 0 | 0 | — | — |
| Sprangletop | 0 | 0 | 2 | 0 | 1 | 0 | — | — |

TABLE 3

Pre-emergence Herbicidal Activity
Compounds A and B

| | Rate of Application (lbs./acre) | | | | | | | |
|---|---|---|---|---|---|---|---|---|
| | 2.0 | | 1.5 | | 1.0 | | 0.5 | |
| Plant | A | B | A | B | A | B | A | B |
| Velvetleaf | 10 | 6.7 | 10 | 7.3 | 10 | 5.7 | 9.7 | 3.3 |
| Sicklepod | 10 | 8 | 9.7 | 5.7 | 9 | 3.7 | 8 | 2 |
| Morningglory | 10 | 1.3 | 9.3 | 1 | 8.3 | 1 | 4.3 | 0 |
| Safflower | 10 | 2 | 8.3 | 2.3 | 5.7 | 1 | 4.3 | 0.3 |
| Hemp Sesbania | 10 | 6 | 10 | 6 | 9.7 | 2.7 | 9.3 | 0.3 |
| Barnyardgrass | 9.7 | 5.3 | 9.7 | 4.7 | 8.3 | 3.3 | 6 | 1.3 |
| Black Nightshade | 10 | 9 | 10 | 7.7 | 10 | 7.3 | 10 | 6.3 |
| Prickly Sida | 10 | 8 | 10 | 6 | 10 | 5.3 | 8 | 1.3 |
| Yellow Foxtail | 9.7 | 6.7 | 9.7 | 4.3 | 8.3 | 4.3 | 6.3 | 2.7 |
| Jimsonweed | 10 | 4.7 | 10 | 4.7 | 9.7 | 3.7 | 9.3 | 2.7 |
| Shattercane | 9.3 | 3.3 | 9 | 2.3 | 6.3 | 1 | 4 | 1 |
| Bindweed | 10 | 4 | 8.3 | 3.7 | 8.3 | 2.7 | 6.3 | 0 |
| Broadleaf Signalgrass | 9.7 | 6.3 | 9.3 | 5 | 7.7 | 2 | 7 | 2 |
| Buckwheat | 9.0 | 5 | 10 | 2.7 | 7.3 | 1.7 | 6 | 0 |
| Cocklebur | 6.3 | 4.7 | 6.7 | 2.7 | 5.3 | 2.7 | 3.7 | 0.3 |
| Sorghum | 4.7 | 1.3 | 4.7 | 3 | 2.7 | 2.3 | 1 | 0 |
| Corn | 0 | 0 | 0 | 0.3 | 0 | 0 | 0 | 0 |

As shown in Tables 1 and 2, the Compounds A and C of the invention are indicated by Table 2 to be slightly inferior to PROBE ® by post-emergence but are both overwhelmingly superior to the dichloro analogue Compound D. From the data in Table 1 it is clearly seen that both Compounds A and C of the invention are distinctly superior on pre-emergence application to not only the dichloro analogue Compound D but also to PROBE ® (Compound B), such superiority indicating that the fluorine-substitution in accordance with the invention surprisingly results in a substantially more potent herbicidal activity and/or a substantially broader spectrum of high herbicidal activity.

In Table 3 the clear superiority of Compound A of the invention over the commercial candidate PROBE ® on pre-emergence application is confirmed and even better realized in field testing in a somewhat different and particularly significant variety of weeds, yet it is also noted that corn is left substantailly undamaged by Compound A at all application rates.

What is claimed is:

1. The compound of the formula:

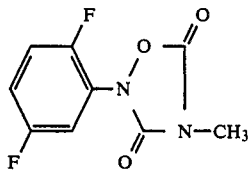

2. The method of combatting weeds in a locus containing weeds comprising applying to such locus a herbicidally effective amount of the compound of claim 1.

3. The method of claim 5 in which said locus comprises both weeds and a crop and the compound is applied at a rate herbicidally effective to weeds therein and ineffective to substantially damage said crop.

4. The method of claim 2 in which the compound is applied pre-emergent the weeds.

5. The method of claim 6 in which the compound is applied pre-emergent the weeds and crop.

6. The method of claim 5 in which the crop is corn.

7. The method of claim 5 in which the crop is rice.

8. The method of claim 5 in which the crop is sorghum.

9. An agricultural composition comprising an inert carrier and a herbicidally effective amount of the compound of claim 1.

10. The method of claim 6 in which the crop is cotton.

* * * * *